United States Patent [19]

Wolf

[11] 4,011,457

[45] Mar. 8, 1977

[54] WEB DEFECT MONITOR FOR ABRUPT CHANGES IN WEB DENSITY

[75] Inventor: William Edward Wolf, Newark, Del.

[73] Assignee: E. I. Du Pont de Nemours and Company, Wilmington, Del.

[22] Filed: Aug. 6, 1975

[21] Appl. No.: 602,465

[52] U.S. Cl. .................. 250/563; 250/214 RC; 356/200

[51] Int. Cl.² ...................... G01N 21/32

[58] Field of Search .......... 230/561, 562, 563, 571, 230/572, 214 R, 214 RC; 209/111.7; 356/199, 200, 237

[56] References Cited

UNITED STATES PATENTS

| | | | |
|---|---|---|---|
| 2,812,447 | 11/1957 | MacMartin et al. | 250/563 |
| 3,056,032 | 9/1962 | Cannon | 250/563 |
| 3,257,563 | 6/1966 | Laurent | 250/563 |
| 3,389,789 | 6/1968 | Watson et al. | 250/563 |

Primary Examiner—David C. Nelms

[57] ABSTRACT

An electro-optical scanner for detecting variations in a web and generating output signals representative of the variations is provided with discriminator logic and alarm circuitry that indicates when the output signals shift from a value exceeding a predetermined positive (negative) threshold value to a value beyond a predetermined negative (positive) threshold value within a prescribed minimum period of time as an occurrence of an abrupt change in web density and processing circuitry for determining and indicating when the number of such occurrences per unit time exceeds a threshold or predetermined number.

5 Claims, 12 Drawing Figures

FIG. 2
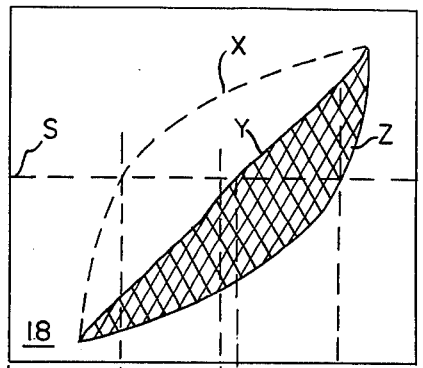
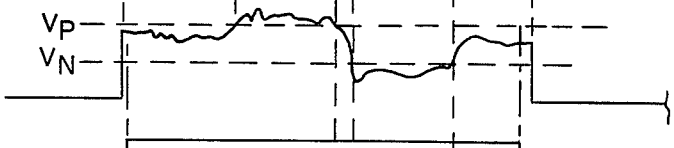
FIG. 3A
FIG. 3B
FIG. 3C
FIG. 3D
FIG. 3E
FIG. 3F
FIG. 3G
FIG. 3H
FIG. 3I
FIG. 3J

WEB DEFECT MONITOR FOR ABRUPT CHANGES IN WEB DENSITY

BACKGROUND OF THE INVENTION

This invention concerns detecting defects occurring in nonwoven webs and more particularly concerns a web inspection system and method for detecting and extracting signals by an abrupt change in web density from a noisy product scan signal characterstic of good product.

This defect monitoring system is particularly suitable for webs manufactured by the process taught by Kinney in U.S. Pat. No. 3,338,992 but is not restricted thereto. The type of web defects to which this device is particularly applicable includes those formed by a malfunctioning pneumatic laydown jet as it deposits filaments onto a receiver. These defects are sometimes referred to as "blow arounds" or "jet hangs" and are formed when a jet either forces a mass of filaments to be deposited away from its normal location or when a mass of fibers temporarily holds up in the jet and is then deposited in a dense mass on the web-forming filament receiver. All of the defects of this type are characterized by an abrupt change in web density with the resulting appearance of a sharply defined light or dark blotch when viewed either by transmitted or reflected light. Since an acceptable web with no defects has by its very nature of randomly deposited filaments, a short range, uneven structure, a signal produced by a conventional electro-optical scanner such as disclosed in U.S. Pat. No. 3,866,054 of this acceptable web will contain a high level of rapidly changing peaks and valleys. This high background noise signal has in the past effectively masked the onset of the abrupt edge defects even when analyzed by discriminator circuitry employing conventional differentiation. Thus abrupt edge defects have not been detectable by known automatic inspection devices heretofore even though flaws of this type are easily identifiable visually because of their relatively large size and contrast with the surrounding material.

SUMMARY OF THE INVENTION

This invention comprises an improved flying spot inspection system for web materials that includes a radiation source such as a laser, a means for traversing a beam of radiation from this source across the web and across a photocell adjacent one side of the web, a light pipe arranged to collect radiation from this beam after it has either passed through or has been reflected by the web and photoelectric means arranged to receive the thus collected light and provide an electrical signal characteristic of the variations in reflectivity or transmissivity of the web. The improvement includes a product gate generator which receives its input signal from the first mentioned photocell and provides an enabling pulse signal to first and second AND gates. First and second signal discriminators are separately connected to the other input terminal of the first and second AND gates respectively, and arranged to provide respective input pulses to these gates when the product signal amplitude exceeds a predetermined upper level or goes blow a predetermined lower level. First and second one shot multivibrator pairs are connected to the output terminals of first and second AND gates in order to produce data pulses to corresponding first and second flip-flop circuits. However, each AND gate output terminal is also cross connected to the other flip-flop in order to furnish clock counts to operate these flip-flops only when a concurrent transition of the signal amplitude across the other predetermined level occurs. The outputs of the latter are connected to a processing circuit which separately counts the low to high and high to low edge discontinuities which occur per unit time and produces an alarm when either count exceeds preset values. In other words, the improvement comprises a logic circuit which presents a defect pulse signal each time the trailing edge of an output pulse generated by a positive (negative) threshold discriminator and the leading edge of the corresponding output pulse from a negative (positive) threshold discriminator fall within a predetermined time interval as determined by the characteristics of one shot multivibrator circuits.

Thus, this combination of discriminator and logic circuitry provides an output defect signal independent of normal product noise when the signal output shifts amplitude, i.e., makes a transition, from a value exceeding a predetermined positive (negative) threshold to a value beyond a predetermined negative (positive) threshold within a prescribed minimum length of time. In addition, the duration of the defect signal pulse provides a measure of the abruptness of the edge discontinuity.

BRIEF DESCRIPTION OF THE DRAWINGS

FIG. 2 is a schematic representation of an objecttionable abrupt edge defect within a portion of web being scanned; and FIGS. 3A–3J show signal wave forms appearing at appropriate points A-J in FIG. 1 and drawn to a scale corresponding to the rate of scan across the sample area so that FIGS. 2 and 3 are coordinated by vertical lines relating scan positions to time during signals.

DETAILED DESCRIPTION OF THE PREFERRED EMBODIMENT

Figure 1:
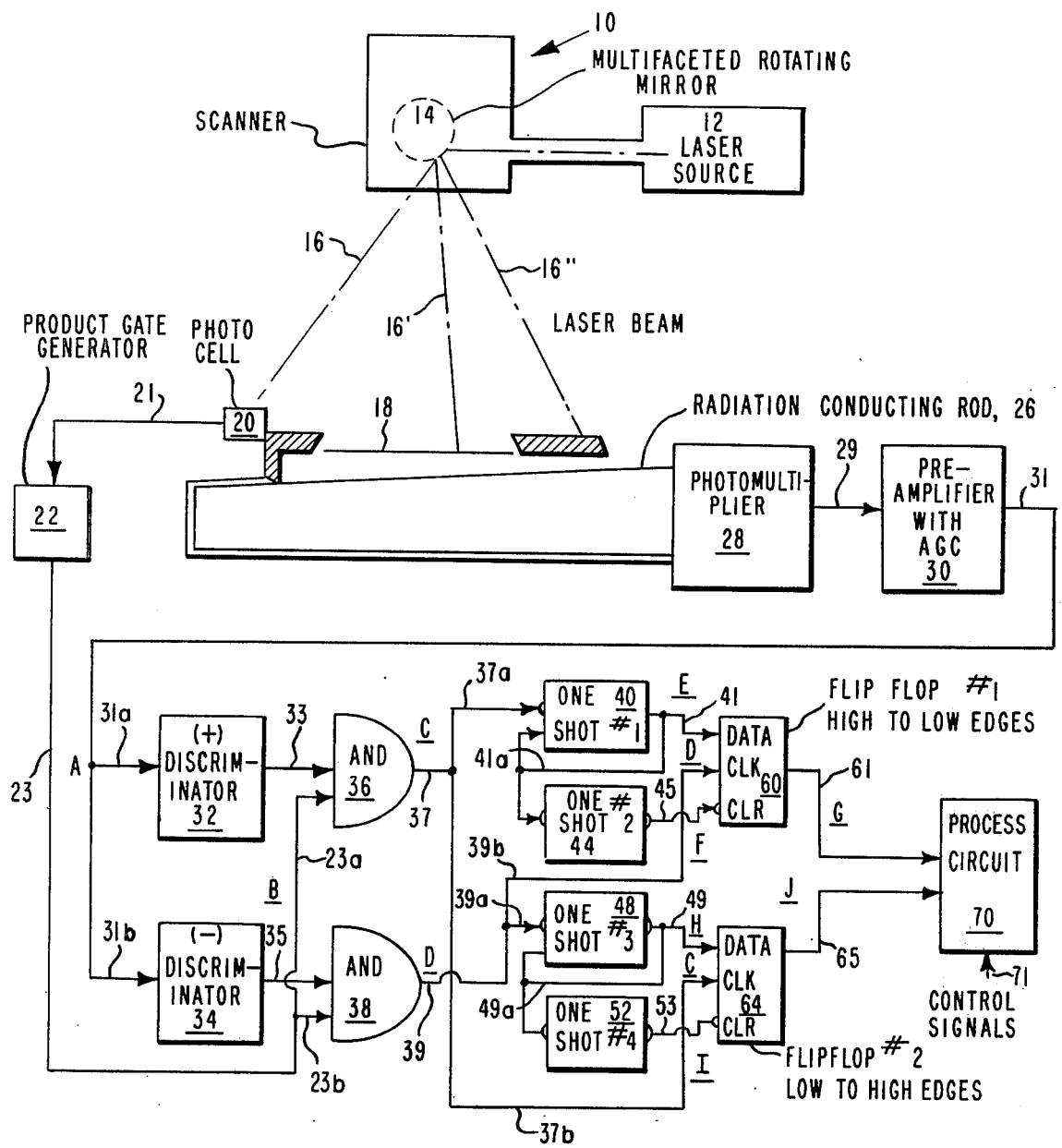
FIG. 1 is an elevational view of a flying spot web inspection device in a transmission mode configuration having attached thereto circuitry shown as a block diagram.

Referring first to FIG. 1, the flying spot scanner chosen for purposes of illustration is denoted gnerally as 10 and includes a laser source 12 directed toward a multifaceted rotating mirror 14 which, with associated beam forming optics (not shown), produces a highly collimated scanning radiation beam. This beam, shown in three positions 16, 16', 16", sweeps a spot of radiation transversely across the running product web 18 at a high enough velocity to insure that successive scans overlap sufficiently for complete product inspection.

At the start of each scan, the beam passes over photocell 20 which is connected over line 21 as the input to gate generator 22, the output of which is passed over line 23 and is connected via lines 233a and 23b to first input terminals of AND gates 36, and 38, respectively. Gates 36 and 38 are typically type SN-74HO8 manufactured by Texas Instruments Company.

A radiation conducting rod 26 conveys transmitted radiation (which has passed from the laser beam 16 through web 18) to a photomultiplier (PM) tube 28. The output of PM-28, which will be referred to as the product signal, is connected over line 29 to a conventional preamplifier -AGC circuit 30 and is then passed to first and second discriminator circuits 32, 34 over line 31 and branch lines 31a and 31b, respectively. The output of discriminator 32 passes over line 33 to form the second input for AND gate 36; the output from discriminator 34 similarly passes over line 35 to form the second input of AND gate 38. These discriminators 32, 34 are typically type SN-72820, manufactured by Texas Instruments Company. The output of gate 36 is connected first over lines 37, 37a to a first one shot 40 and also over lines 37, 37b, to the clock terminal of a first flip-flop circuit 64. The output of one shot 40 extends over line 41 to the data input terminal of a second flip-flop 60. Similarly, the output from gate 38 extends over lines 39, 39a to the input terminal of a second one shot 48 and at the same time over lines 39, 39b to the clock terminal of the second flip-flop circuit 60. The output of second one shot 48 connects over line 49 to the data input terminal of first flip-flop 64. A branch line 41a extends from the output of one shot 40 to its reset terminal and to the input terminal of a third one shot 44, the output of one shot 44 is furnished over line 45 to the clear terminal of flip-flop 60. Similarly, a reset line 49a extends from the output of one shot 48 to its reset terminal and to a fourth one shot 52, the output of which is connected over line 53 to the clear, terminal of flip-flop 64. The output of the flip-flop 60 extends over line 61 to a first input terminal of processing circuit 70 whereas the output of flip-flop 64 is connected over line 65 to the other input terminal of component 70 thus completing the circuitry.

In the above circuit components, the one shots 40, 44, 48, 52 are typically Type 9602 manufactured by Fairchild, and the flip-flops 60, 64 are SN-7474, both manufactured by the Texas Instruments Company. In processing circuit 70 which comprises one or more counters and comparators which first total the edge signals per unit then compares the edge counts to threshold and generates a reject signal when the number of edge counts exceeds preset threshold, the counters are typically model M236 and the comparators are model M168 both by Digital Equipment Corporation.

The letters A-J are located on FIG. 1 adjacent the appropriate points where the signals shown in FIGS. 3A-3J are to be found.

The operation of this device is now described in connection with the detection of a single abrupt edge defect within the scan of the laser beam in the transmission mode configuration such as that shown schematically in FIG. 2. Specifically, this defect is one wherein the scan traverses an area of low density followed by a rapid change to a high density section both bordered by regions of acceptable density. Thus, in FIG. 2 the scan line is designated by the dashed line S which scans the web 18 over a region of acceptable density until it hits the dashed curve X where it gradually blends into a region of light density until the scan reaches curve Y where there is an abrupt change to high density region which tapers off until it reaches curve Z after which the scan passes over a further region of normal density. The product signal for this particular scan which appears at A in FIG. 1, is shown by the pedestal signal of FIG. 3A. The two horizontal dashed lines in FIG. 3A which are labeled $V_P$ and $V_N$, respectively, represent the positive and negative threshold signal levels for the two discriminators 32 and 34, respectively. These thresholds are chosen so that signals from materials of acceptable density normally fall between these two thresholds whereas material with density lower than the acceptable limit provides signals which extend above the line $V_P$ (corresponds to the region in this example between lines X and Y of FIG. 2). Similarly, the material of higher than acceptable density gives signals that pass below the level of line $V_N$ (corresponds to the region between curve Y and Z on FIG. 2).

The pulse signal of FIG. 3B represents the output of product gate generator 22 and is a pulse whose leading and trailing edges fall just inside the leading and trailing edge of the product pedestal signal of FIG. 3A. This gate pulse signal functions to exclude false signals that may be generated by the scan of the two sides of the web, by controlling the discriminator 32, 34 output signals appearing at input terminals of AND gates 36, 38.

The pulse shown in FIG. 3C produced by discriminator 32 starts at the time the scan passes curve X and terminates when it arrives just short of curve Y, thus, representing the time during which the product signal exceeds the threshold level $V_P$. Similarly, the signal of FIG. 3D represents a pulse starting when the product signal extends below $V_N$ and lasts until just short of the time the signal again passes into the normal region. The pulse of FIG. 3D represents the region between curves Y and Z of FIG. 2.

The pulse signal of FIG. 3E represents the output of one shot 40 which is triggered by the trailing edge of signal 3C. The duration of the pulse of FIG. 3E is determined by the characteristics of one shot 40. This signal will actuate flip-flop 60 if and only if a clock signal is received over line 39b by virtue of the leading edge of pulse of FIG. 3D occurring within the time interval $\Delta T_P$, which is the preset duration of the pulse of FIG. 3E. Thus, when the trailing edge of a signal excursion beyond the threshold of one discriminator (here the $V_P$ of discriminator 32) occurs within a predetermined time interval before the leading edge of an excursion beyond the threshold level of the other discriminator ($V_N$ in this example), a pulse, shown by FIG. 3G, is provided to processing circuit 70 that, in turn, actuates an alarm if a count of these pulses per unit time exceeds a threshold or predetermined number. The pulse of FIG. 3H represents the output of one shot 48 which would be used to provide a defect signal if a positive excursion were to occur thereafter during the time interval $\Delta T_N$, the preset width of the pulse of FIG. 3H.

In order to reset the two flip-flops, one shots 44 and 52 are provided to give the pulse signals shown by FIGS. 3F and 3I. These one shots are fired by the trailing edges of the pulses of FIG. 3E and of FIG. 3H, respectively, thus, resetting both flip-flops, in preparation for the next defective scan.

The above circuitry provides for a defect signal (waveform 3G) when the product signal first undergoes an excursion beyond a positive threshold and then passes beyond a negative threshold within a preselected interval of time $\Delta T_P$. It is evident that, if the excursions had been reversed in order, the signal would have been produced over line 65 giving rise to an equivalent defect signal. (Waveform 3J illustrates the case where no such excursions were detected). Furthermore, since both signal excursions can be detected within the same product scan, the product may be monitored for the existence of multiple types of abrupt edged defects. In summary, this defect monitoring is achieved by an action which is analagous to a digital differentiation since a defect signal is produced only if the product pedestal signal voltage amplitude swings between values greater than $V_P$ and less than $V_N$ when this occurs during either fixed time interval $\Delta T_P$, waveform 3E or $\Delta T_N$, waveform 3H, having durations preset in the respective one shots. In other words when $\Delta V/\Delta T > K$, where K is a preselected constant rate and $\Delta V$ spans $V_P$ and $V_N$. The apparatus determines a potential defect but avoids false reject signals which would arise in conventional analog differentiating circuitry when signal level change rates of comparable magnitude occur as a result of scans across acceptable product.

Thus, sharp edged defects such as "blow arounds" and "jet hangs" in spunbonded webs may be detected in spite of large random web density variability.

The separate edge signals (waveforms G,J) are then processed by the processing circuit 70. This circuit comprises one or more counters and comparators which first total the edge signals per unit time. Then these edge counts are compared to edge count thresholds and reject signals are generated whenever the number of edge discontinuities per unit time exceeds a predetermined number, i.e., preset thresholds. Signals from positive-to-negative transitions are processed separately from negative-to-positive signals. Control signals introduced into circuit 70 at 71 are used to set the time interval during which counts are made.

What is claimed is:

1. In a method of inspecting a web that includes detecting density variations in the web by electrooptically scanning the web and generating output signals representative of said variations, the improvement comprising: generating signals when the amplitudes of said output signals exceed predetermined positive and negative threshold levels in either order of occurrence; and indicating when an output signal exceeding one of said threshold levels changes in level and exceeds the other threshold level within a predetermined period of time.

2. In a method of inspecting a web that includes detecting density variations in the web by electro-optically scanning the web and generating electrical output signals representative of said variations, the improvement comprising: generating a pulse when the amplitude of said output signals exceeds sequentially predetermined positive and negative threshold levels in either order of occurrence within a predetermined period of time; counting the pulses generated per unit time; and indicating when the number of pulses per unit of time exceed a predetermined number.

3. The method as defined in claim 2, including the step of generating a pulse when an output signal exceeding one of said threshold levels changes in level and exceeds the other threshold level within a predetermined period of time and measuring the duration of said pulse to provide a measure of the abruptness of said density variation.

4. In an inspection system for webs that includes means scanning the web for detecting variations in the web and generating output signals representative of said variations, the improvement comprising: discriminator circuitry actuated by said output signals for generating potential defect signals when the amplitudes of said output signals exceed predetermined positive and negative threshold levels in either order of occurrence and means for indicating when an output signal exceeding one of said threshold levels changes in level and exceeds the other threshold level within a predetermined period of time.

5. In an inspection system for webs that includes means scanning the web for detecting variations in the web and generating output signals representative of said variations, the improvement comprising: discriminator circuitry actuated by said output signals for generating potential defect signals when the amplitudes of said output signals exceed predetermined positive and negative threshold levels in either order of occurrence; and means for determining transitions of output signals exceeding one of said threshold levels and then exceeding the other threshold level within a predetermined period of time.

* * * * *